United States Patent [19]

Vanlerberghe et al.

[11] 4,416,868
[45] Nov. 22, 1983

[54] COSMETIC EXCIPIENT

[75] Inventors: Guy Vanlerberghe, Montjay-la-Tour; Henri Sebag, Paris, both of France

[73] Assignee: Societe Anonyme dite: L'Oreal, Paris, France

[21] Appl. No.: 602,962

[22] Filed: Aug. 8, 1975

[30] Foreign Application Priority Data

Aug. 12, 1974 [LU] Luxembourg .......................... 70720

[51] Int. Cl.³ .................... A61K 7/042; A61K 7/021; A61K 7/025
[52] U.S. Cl. ........................................ 424/59; 424/47; 424/60; 424/63; 424/64; 424/65; 424/68; 424/70; 424/341; 424/343; 424/358; 424/365; 260/410.9 R; 560/265; 568/613
[58] Field of Search .................... 424/64, 60, 59, 341, 424/343; 260/484, 614, 615

[56] References Cited

U.S. PATENT DOCUMENTS

| | | | |
|---|---|---|---|
| 1,927,295 | 9/1933 | Powers | 260/484 A |
| 1,959,930 | 5/1934 | Schmidt et al. | 260/615 B |
| 1,970,578 | 2/1934 | Schoeller et al. | 260/615 B |
| 2,025,984 | 12/1935 | Harris | 260/484 A |
| 2,089,569 | 8/1937 | Onthner et al. | 260/615 B |
| 2,228,929 | 1/1941 | Reibnitz | 260/615 B X |
| 2,236,517 | 4/1941 | Cahn et al. | 260/484 X |
| 2,248,089 | 7/1941 | Katzman et al. | 424/341 X |
| 2,457,139 | 12/1948 | Fife et al. | 424/343 X |
| 2,467,884 | 4/1949 | Elias | 424/343 X |
| 2,583,576 | 1/1952 | Kern et al. | 424/343 X |
| 3,642,980 | 2/1972 | Lachampt et al. | 424/64 |
| 3,666,671 | 5/1972 | Kalopissis et al. | 424/64 |
| 3,745,033 | 7/1973 | Hutchison | 424/64 |
| 3,835,169 | 9/1974 | Kraft et al. | 424/64 |
| 3,846,556 | 11/1974 | Handjani et al. | 424/64 |
| 3,865,542 | 2/1975 | Kalopissis et al. | 424/64 |
| 3,877,955 | 4/1975 | Kalopissis | 424/64 |
| 3,890,358 | 6/1975 | Hutchison et al. | 424/64 |
| 3,911,105 | 10/1975 | Papantoniou et al. | 424/64 |
| 3,937,811 | 2/1976 | Papantoniou et al. | 424/64 |

*Primary Examiner*—Dale R. Ore
*Attorney, Agent, or Firm*—Cushman, Darby & Cushman

[57] ABSTRACT

A cosmetic excipient comprises a compound or mixture thereof having the formula

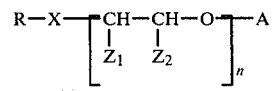

wherein R is alkyl having 7-20 carbon atoms, a mixture of said alkyl radicals, the hydrocarbon residue of lanolin when X is oxygen or the hydrocarbon residue of lanolic acid when X is

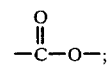

one of $Z_1$ and $Z_2$ represents —CH$_2$—Y—R' and the other represents hydrogen; X represents oxygen or carbonyloxy of the formula

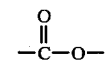

linked to R through the free bond of the carbon atom of the carbonyloxy group; Y represents —CH$_2$—, oxygen and carbonyloxy of the formula

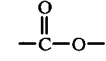

linked to R' through the free bond of the carbon atom of the carbonyloxy group R' represents alkyl having 3-30 carbon atoms or a mixture of said alkyl radicals, or a portion of the —Y—R' groups can represent —OH; A is hydrogen or when Y is carbonyloxy a mixture of hydrogen and

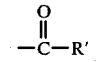

wherein R' has the meaning given above; and n is a decimal or whole number greater than 1 and lower than or equal to 10.

28 Claims, No Drawings

COSMETIC EXCIPIENT

The present invention relates to cosmetic excipients.

Heretofore, a great number of oils have been proposed for use as excipients in cosmetic compositions. However, several among them exhibit some disadvantages. For instance, the animal or vegetable oils, or their derivatives, are susceptible of becoming rancid due to oxidation of unsaturated components contained therein. Moreover their ready availability in quantities required is often questionable due to seasonal variations in the growing of the vegetable oil sources and to the depletion of certain species, for example, sharks which constitute a source of animal based oils.

It has also been found that synthetic oils, such as for example, branched fatty alcohols or esters of fatty acids and short chain alcohols, which have also been proposed for use as cosmetic excipients, are difficult to emulsify or at least lack the ability to impart a smooth feel to the skin. Besides they tend to penetrate too rapidly when spread on the skin which is a serious disadvantage when they are formulated in cosmetic compositions for application to dry skin. It is also known that petrolatum oils exhibit poor spreading qualities and they generally leave on the skin an oily film which, of course, is generally undesirable.

It has now been found that certain polyethers, which can be represented by general formula I below, do not exhibit the above disadvantages of previously known oils, natural or synthetic, and can advantageously be employed as a cosmetic excipient.

The cosmetic excipient of the present invention is generally present in the form of an oil or a wax having a relatively low melting point. Since the cosmetic excipient of the present invention is a saturated product, it does not become rancid. Further the product of the present invention exhibits highly favorable spreading characteristics on human skin and after application, the skin has a soft and smooth feel and does not have an oily film thereon.

The compounds of the present invention have a molecular weight ranging between about 300 and 5,000 and those having a molecular weight near the middle of this range provide cosmetic products exhibiting particularly desirable skin penetrating characteristics.

The compounds of the present invention are odorless and generally colorless, although some exhibit a slightly yellow or amber coloration. They are miscible or compatible with a great number of oils, waxes, solvents, emulsifying agents or perfumes generally employed in cosmetic compositions which facilitates their incorporation into such compositions.

Thus, the present invention relates to the use as a cosmetic excipient of a compound or mixture thereof, said compound having the formula

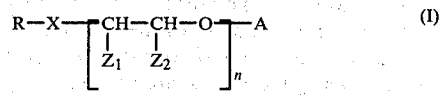

wherein R is selected from the group consisting of alkyl having from 7 to 20 carbon atoms, a mixture of said alkyl radicals, a hydrocarbon residue of lanolin alcohol when X is oxygen and a hydrocarbon residue of lanolic acid when X is

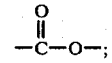

one of the substituents $Z_1$ and $Z_2$ represents $-CH_2-Y-R'$ and the other represents hydrogen; X represents a member selected from the group consisting of oxygen and carbonyloxy of the formula

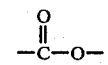

linked to R through the free bond of the carbon atom of said carbonyloxy group; Y represents a member selected from the group consisting of $-CH_2-$, oxygen or carbonyloxy of the formula

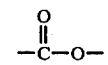

linked to R' through the free bond of the carbon atom of said carbonyloxy group, R' represents a member selected from the group consisting of alkyl having 3 to 20 carbon atoms and a mixture of said alkyl radicals, or a portion of the $-Y-R'$ groups can represents $-OH$; A is selected from the group consisting of hydrogen and when Y is carbonyloxy a mixture of hydrogen and

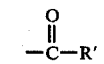

and n is a whole or decimal number greater than 1 and lower or equal to 10.

In the embodiment of the invention where a portion of the $-YR'$ groups represents $-OH$, the weight of the units

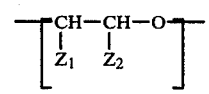

containing said $-YR'$ as OH represents at a maximum 20% of the total weight of all the

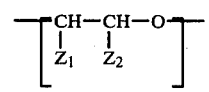

units.

The alkyl values of R and R' can be linear or branched and preferably at least one of R and R' is branched alkyl.

The compounds of formula I are obtained by polyaddition of alkylene oxides, or of glycidyl ethers or esters on a ROH alcohol having a number of carbon atoms greater than or equal to 7 or on a R—COOH acid having a number of carbon atoms greater than or equal to 8. Preferably, the R—OH alcohol has a number of carbon atoms greater than or equal to 8.

In the compound or mixture of compounds of formula (I), R represents principally a hydrocarbon residue derived:

(a) from a R—OH alcohol such as octanol, decanol, dodecanol, tetradecanol, hexadecanol, octadecanol, eicosanol, 2-ethyl hexanol, 2,2-dimethyl hexanol, 3,7-dimethyl octanol, 2-hexyl decanol, 2-octyl-decanol, 2-octyl dodecanol, isostearyl alcohol, hexadecyl alcohol or mixtures of these alcohols, or a mixture of commercial oxo type alcohols such as Dobanol 25 (a mixture of undecyl, dodecyl, tridecyl, tetradecyl, and pentadecyl alcohols) or Sidopol 16 sold by Sinnova, or lanolin alcohol sold under the name Satulan, or (b) from a R—COOH acid such as octanoic, decanoic, dodecanoic, tetradecanoic, hexadecanoic, octadecanoic, eicosanoic, 2-ethyl hexanoic, 2-ethyl-2-methyl hexanoic, 3,5,5-trimethyl hexanoic, neo-tridecanoic, isopalmitic, isostearic or mixtures of these acids, or lanolic acid.

In the compound, or mixture of compounds of formula (I) R' represents principally:

(a) a hydrocarbon radical such as propyl, butyl, pentyl, hexyl, heptyl, octyl, nonyl, decyl, undecyl, dodecyl, tridecyl, tetradecyl, hexadecyl, or a mixture thereof;

(b) the hydrocarbon residue of a R'—OH alcohol such as isopropanol, tert-butanol, isopentanol, 2-ethyl butanol, 2-methyl pentanol, 4-methyl pentanol, as well as those alcohols mentioned above for the value of R except lanolin alcohol; and (c) the hydrocarbon residue of a R'—COOH acids such as those mentioned above for the value of R except lanolic acid.

In formula I, the number "n" can be defined as the average degree of polymerization and corresponds to the number of epoxide molecules used by the molecule of the R—OH alcohol or the R—COOH acid, which explains why n can be a whole or decimal number. It corresponds to an average degree of polymerization that is the compounds of formula I can exist individually, which compounds have a lower or higher degree of polymerization, "n" representing an arithmetic average.

By "neo-tridecanoic acid" is meant a mixture of isomers having branched chains of tridecanoic acid and by lanolic acid is meant the acids obtained by hydrolysis of lanolin, which acids comprise a mixture of fatty acids, particularly aliphatic acids, substituted or not, as well as hydroxylated acids. An example of lanolic acid is one sold by Croda having a saponification index of 174 and an iodine index of 22.

Principal among the compounds of formula I are those having the formula

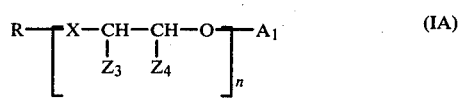   (IA)

wherein R, X and n have the meaning given above; one of $Z_3$ and $Z_4$ represents hydrogen and the other represents —$CH_2$—$Y_1$—$R'_1$ wherein $Y_1$ represents a member selected from the group consisting of —$CH_2$—, oxygen and carbonyloxy of the formula

linked to $R'_1$ through the free bond of the carbon atom of said carbonyloxy group, $R'_1$ represents a member selected from the group consisting of alkyl having from 7 to 20 carbon atoms and a mixture of said alkyl radicals, or a portion of the —$Y_1$—$R'_1$ groups can represent —OH; $A_1$ is selected from the group consisting of hydrogen and when $Y_1$ is carbonyloxy, a mixture of hydrogen and

Preferably $R'_1$ represents alkyl containing 8 to 20 carbon atoms.

The present invention also relates to a compound or mixture thereof having formula IA.

More particularly the present invention relates to the cosmetic excipients of formula I described hereafter in Examples 1-29, and to the compounds described in Examples 1-10, 13-18 and 20-29.

To prepare the compounds of formula I, wherein A is hydrogen, a compound having the formula

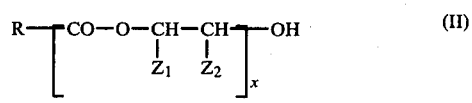   (II)

wherein R, $Z_1$ and $Z_2$ have the meaning given above and x is a whole number equal to 0 or 1 is reacted with a compound having the formula

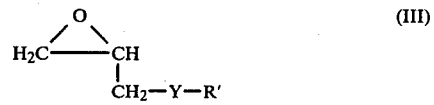   (III)

wherein Y and R' have the meaning given above, the molar ratio of compound III to compound II being y:1 wherein y is a number equal to (n-x), n having the meaning given above.

The reaction is carried out in the presence of a Lewis acid catalyst, for example, $BF_3$, $SnCl_4$ or $SbCl_5$. Generally the reaction is effected without a solvent although a solvent which is inert with respect to the reactants can be employed. The reaction temperature ranges between 50° and 120° C. and preferably between 60° and 90° C.

In the presence of Lewis acids, the opening of the epoxide is not unequivocal and the following two isomeric arrangements (A) and (B), of the unit between the brackets of formula I can be obtained:

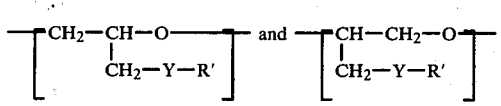

(A)   (B)

The relative proportion of these two isomeric arrangements (A) and (B) is quite difficult to estimate. It is also difficult to direct the epoxide opening reaction to favor one or the other of these arrangements. The compounds of the present invention represented by formula I are then, generally, a mixture of arrangements (A) and (B).

The reactants of formula II wherein x=1 can themselves be prepared by reacting a molecule of a R—COOH acid with a molecule of an epoxide of formula III, in the presence of a basic catalyst, for example an alkaline alcoholate such as sodium or potassium methylate, or a tertiary amine such as triethyl amine or N,N'-tetramethyldiamino butane, or even in the presence of a metallic soap, comprising principally an alkali or alkaline earth salt of a fatty acid. This reaction is generally carried out at a temperature between 125° and 135° C. for about 2 to 6 hours. The basic catalyst is neutralized with hydrochloric acid and the reaction mass is eventually washed with water and dried by heating under reduced pressure to remove all traces of water, thus yielding a compound of formula II ($x=1$). Thereafter a Lewis acid catalyst can be added and the above described polyaddition reaction with the epoxide of formula III as indicated above is effected so as to obtain a compound of formula I, wherein A is hydrogen.

The molar proportions of acid or basic catalyst used in the above processes can vary from 0.2 to 10% relative to the ROH alcohol or RCOOH acid.

After the polyaddition of the compound of formula III with the compound of formula II, the products obtained are generally neutralized, washed with water and dried. The ultimate elimination of all traces of volatile material or non-condensed reactants can be effected by molecular distillation.

The present invention also relates to a process for preparing compounds of formula IA comprising reacting a compound having the formula:

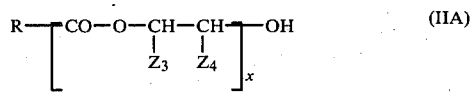 (IIA)

with a compound of the formula

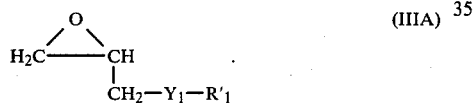 (IIIA)

The reaction conditions employed are essentially the same as those described above for the preparation of compounds of formula I.

As indicated above, products represented by formula IA can also contain the following two isomeric arrangements for the unit defined between the brackets in the structural formula IA:

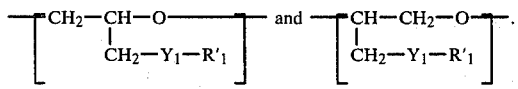

The formula IIA reactant wherein $x=1$ can be prepared by reacting a molecular of R—COOH acid with a molecule of an epoxide of the formula IIIA, the operating conditions for this reaction being those described above.

According to the present invention, compounds of formula I wherein Y represents

can also be prepared:

(1) either by direct esterification, with the aid of a R'—COOH acid, of a polyhydroxylated polyether of formula IV:

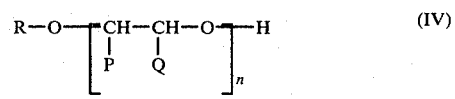 (IV)

wherein n and R have the meanings given above, and one of the substituents P and Q represent hydrogen while the other represents —CH$_2$OH.

Compounds of formula IV in turn can be prepared in accordance with procedures described in French Pat. No. 1,477,048.

The esterification with the aid of a R'—COOH acid can be partial or total, whereby, on the one hand there can be produced some compounds having the following two units

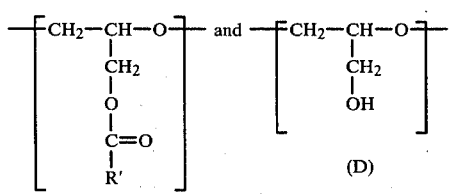

and, on the other hand, there can be produced a mixture of compounds wherein A is hydrogen and compounds wherein A represents the

However, the R'—COOH acid is used in a quantity sufficient so that the weight of units D does not represent more than 20% of the total weight of units (C+D):

or (2) by reacting a R'—COOH acid with tert-butoxy derivative of the formula

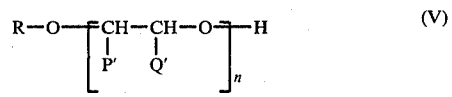 (V)

wherein R and n have the meanings given in formula I and one of P' and Q' represents hydrogen and the other represents

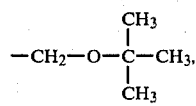

in the presence of a strong protonic acid such as paratoluene sulfonic acid, sulfuric acid or methane sulfonic acid.

Compounds of formula V can be provided in accordance with procedures described in French Pat. No. 2,027,585.

The reaction of the R'COOH acid and the compound of formula (V) is carried out at a temperature ranging from 90° to 170° C., and preferably from about 100° to 120° C.

As a result of an incomplete transformation reaction, some tert-butoxy units can exist which are close to the principal form, i.e.

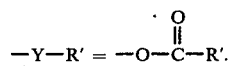

$$-Y-R' = -O-\overset{O}{\underset{\|}{C}}-R'.$$

Further, units of formula (D) such as indicated above, can be formed by hydrolysis which units can be esterified by increasing the heating time. Moreover, the terminal OH groups can be partially or totally esterified.

Of course, the processes of esterifying compounds of formula IV and compounds of formula V can be employed to prepare compounds of IA. These processes for the preparation of compounds of formula IA are also an object of the present invention.

Additionally, the present invention relates to the use of compounds of formula I or IA, or their mixtures, comprising incorporating into a cosmetic composition as an excipient therefor a compound of formula I or IA.

As indicated above, the compounds of formula I or IA which are either oils, or soft waxes, are useful as cosmetic excipients for the production of numerous cosmetic compositions such as milks, creams, emulsions for application to the skin, various makeup products such as lip rouges and cheek rouges, compositions for the bath, products for protection against solar rays, sprays, such as antiperspirants and products for imparting a shiny appearance to the hair.

The present invention also relates to cosmetic compositions containing as an excipient at least one compound of formula I or IA.

In these compositions of the present invention, the compounds of formula I or IA can be used either as the sole excipient, or in admixture with other excipients and when used alone or with other components can comprise the oily phase thereof. The compounds of the present invention can also serve as a solvent for essential oils or perfumes or be employed as opacifiers, plasticizers, brightening agents and the like.

The compounds of formula I or IA in accordance with the invention are generally used in the cosmetic compositions in an amount which can vary to a large degree, which amount can depend upon the type of formulation or composition to be formulated.

This amount, however, is generally between 0.15 and 70 weight percent and preferably between 0.2 and 50 weight percent based on the total weight of the composition.

The cosmetic compositions of the invention which can be prepared in accordance with conventional methods include principally lip rouges, deodorants, eyelid liner or shadow, creams for the face, hands and body, anti-solar creams, makeup remover creams, dye foundation creams, liquid dye foundations, makeup remover milks, anti-solar milks, bath oils or even brightening agents for the hair.

The following non-limiting examples illustrate the invention. Unless otherwise indicated, all parts and percentages are by weight.

EXAMPLE 1

Preparation of a mixture of compounds of general formula I wherein A is hydrogen, R is pentadecyl, R' is 2-ethyl hexyl, X is

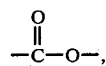

$$-\overset{O}{\underset{\|}{C}}-O-,$$

Y is O and n is 7.

(a) Preparation of an intermediate compound wherein n=1.

To 254 g (1 mole) of molten palmitic acid, there are added 4 g of sodium methylate in methanol under a nitrogen atmosphere. The resulting mixture is heated to a temperature of 110°–120° C. thereby eliminating the methanol. Thereafter 182 g (0.98 mole) of 2-ethyl hexyl glycidyl ether are added dropwise over a 30 minute period. The resulting mixture is then heated for 10 hours at 120° C. at which point the amount of the reaction is 98%.

The excess acid is neutralized with sodium methylate and the reaction mixture is washed twice with 250 ml of water at 85° C. During the course of the first washing, 25 to 30 ml of isopropyl alcohol are added to improve decantation.

After the removal of volatile material, the product is purified by molecular distillation at 170° C. under $10^{-3}$ mm Hg.

(b) To 35.7 g (0.08 mole) of the intermediate compound obtained in step (a) there is added 0.4 ml of a BF$_3$/acetic acid complex containing 33% BF$_3$. The resulting mixture is heated to 75° C. and there are added dropwise 83.7 g (0.45 mole) of 2-ethyl hexyl glycidyl ether over a period of 50 minutes while maintaining the temperature at 75°–80° C. The resulting mixture is then heated for ½ hour at 80° C.

To the reaction mixture there are added with agitation 130 ml of water at 80° C. containing 4.8 g of NaOH (1.2 meq/g). After decantation, the aqueous phase is separated. The organic phase is washed twice with 130 ml of water at 50° C. and then dried by heating under reduced pressure. The volatile products are removed by molecular distillation at 125° C. and the desired product is filtered, yielding a colorless oil having an end liquefaction point of −8° C., an index of refraction at 30° C. of 1.45392, a viscosity at 30° C. of 0.99 poise and a molecular weight, determined by the method of lowering the vapor pressure of 1005.

EXAMPLE 2

Preparation of a mixture of compounds of general formula I wherein A is hydrogen, R represents the hydrocarbon residue of isostearyl alcohol sold under the name Adol 66, R' is octyl, X is oxygen, Y is —CH$_2$— and n=2.3.

To 20.3 g (0.066 mole) of isostearyl alcohol there is added 0.5 ml of BF$_3$/acetic acid complex. The resulting mixture is heated to 75° C. and there are added dropwise 27.6 g (0.15 mole) of 1,2-dodecane oxide in a period of 20 minutes while maintaining the temperature at 70°±5° C. After the addition, the resulting mixture is heated again for 30 minutes at 80° C.

To the reaction mass there are added with agitation 50 ml of water at 95° C. containing 2.5 g of a NaOH solution (1.2 meq/g) and 3 ml of isopropanol. The aqueous phase is separated after decantation. The remaining organic phase which is washed twice with 50 ml of water at 95° C. is then dried by heating under reduced pressure. The volatile products are removed by molecular distillation at 120° C., yielding a yellow oil having an end liquefaction temperature of +10° C., an index of refraction at 30° C. of 1.45875, a viscosity at 30° C. of 0.65 poise and a molecular weight, determined by the method of lowering the vapor pressure, of 665.

EXAMPLE 3

Preparation of a mixture of compounds of general formula I wherein A is hydrogen, R represents the hydrocarbon residue of a branched $C_{16}$ alcohol sold under the name of hexadecyl alcohol, R' is 2-ethyl hexyl, X and Y each represent oxygen and n=4.

To 26 g (0.1 mole) of hexadecyl alcohol dehydrated by heating under a partial vacuum there is added 0.35 ml of a $BF_3$/acetic acid complex containing 33% $BF_3$. The resulting mixture is heated to 75° C. and there are added dropwise 74.5 g (0.4 mole) of 2-ethyl hexyl glycidyl ether in a period of 35 minutes while maintaining the temperature at 75° C.±5° C. The resulting mixture is then heated for 1 hour at 80° C.

To the reaction medium there are added, with agitation, 100 ml of water at 95° C. containing 5.6 g of a NaOH solution (1.2 meq/g).

The aqueous phase is withdrawn after decantation. The organic phase which is washed twice with 100 ml of water is then dried by heating under reduced pressure. The volatile products are removed by molecular distillation at 120° C., yielding an odorless and colorless oil having an end melting point lower than −10° C., an index of refraction at 30° C. of 1.45281 and a molecular weight, determined by the method of lowering the vapor pressure, of 770.

EXAMPLE 4

Preparation of a mixture of compounds of general formula I wherein A is hydrogen, R represents the hydrocarbon residue of isostearyl alcohol sold under the name Adol 66, R' represents 2-ethyl hexyl, X and Y each represent oxygen and n=6.

To 30.5 g (0.1 mole) of isostearyl alcohol there is added 0.5 ml of a $BF_3$/acetic acid complex containing 33% $BF_3$. The resulting mixture is then heated to 75° C. and there are added dropwise 111.6 g (0.6 mole) of 2-ethyl hexyl glycidyl ether in 1 hour while maintaining the temperature at 75°±5° C. After the addition the mixture is heated again for 1 hour at 80° C.

To the reaction mass there are added 125 ml of water at 95° C. containing 9 g of NaOH (1.2 meq/g), to neutralize the catalyst. The aqueous phase is separated after decantation. The organic phase which is washed twice with 125 ml of water is dried by heating under reduced pressure. The unreacted reactants are then removed by molecular distillation at 125° C. under $10^{-3}$ mm Hg and the desired product is filtered on fritted glass, yielding a yellow oil having an end melting point lower than −10° C., an index of refraction at 30° C. of 1.45534 and a molecular weight, determined by lowering the vapor pressure of 895.

EXAMPLE 5

Preparation of a mixture of compounds of general formula I wherein A is hydrogen, R is the hydrocarbon residue of hexadecyl alcohol, R' is a mixture of decyl and dodecyl, X is oxygen, Y is —$CH_2$— and n=3.

To 26 g (0.1 mole) of hexadecyl alcohol there is added 0.50 ml of a $BF_3$/acetic acid complex containing 33% $BF_3$. The resulting mixture is heated to 75° C. and then there are added dropwise in 50 minutes 73.2 g (0.3 mole) of a mixture of $C_{14}$ and $C_{16}$ fatty epoxides. The temperature is maintained at 75° C.±5° C. After the addition, the reaction mixture is heated again at 80° C. for 1 hour.

To the reaction mixture there are added, with agitation, 100 ml of water at 95° C. containing 3.5 g of NaOH solution (1.2 meq/g). The aqueous phase is withdrawn after decantation. The organic phase which is washed with 100 ml of water is then dried by heating under reduced pressure. The unreacted reactants are removed by molecular distillation at 120° C. under $10^{-3}$ mm Hg. The desired product is then filtered hot on fritted glass, which product is a clear colorless liquid at temperatures greater than 30° C. and a semi-crystalline product at ambient temperature. The said product has an index of refraction at 30° C. of 1.45748, a viscosity at 30° C. of 0.97 poise and a molecular weight, determined by the method of lowering the vapor pressure of 730.

EXAMPLE 6

Preparation of a mixture of compounds of general formula I wherein A is hydrogen, R is 2-ethyl hexyl, R' is a mixture of dodecyl and tetradecyl, X and Y are each oxygen and n=6.

To 10.4 g (0.08 mole) of 2-ethyl hexanol there is added 0.38 ml of $BF_3$/acetic acid complex containing 33% $BF_3$. The resulting mixture is heated to 75° C. and then there are added dropwise in 40 minutes 141 g (0.48 mole) of a mixture of $C_{12}$ and $C_{14}$ glycidyl ethers sold under the name of "Epoxide 8" while maintaining the temperature at 75° C.±5° C.

To the reaction mass with agitation there are added 150 ml of water at 95° C. containing 2.5 g of a NaOH solution (1.2 meq/g). After decantation the aqueous phase is withdrawn. The organic phase which is washed with 150 ml of water is then dried by heating under reduced pressure. The unreacted reactants are removed by molecular distillation at 120° C. under $10^{-3}$ mm Hg and the product is filtered on fritted glass, yielding a colorless oil having an end liquefaction temperature of +7° C., an index of refraction at 30° C. of 1.45720, a viscosity at 30° C. of 0.94 poise and a molecular weight, determined by the method of lowering the vapor pressure of 1300.

EXAMPLE 7

Preparation of a mixture of compounds of general formula I wherein A is hydrogen, R represents $C_{12}H_{25}$, R' is 2-ethyl hexyl, X and Y are each oxygen and n=10.

To 9.3 g (0.05 mole) of dodecanol (Alfol 12) there is added 0.50 ml of $BF_3$/acetic acid complex. The resulting mixture is heated to 75° C. and then there are added dropwise in 45 minutes 93 g (0.5 mole) of 2-ethyl hexyl glycidyl ether while maintaining the temperature at 75° C.±5° C.

After the addition, the reaction mass is heated to 80° C. for 1 hour. The absence of the epoxide function is then verified by dosage.

To the reaction mass there are added, with agitation, 100 ml of water at 95° C. containing 6.3 g of a NaOH solution (1.2 meq/g). The aqueous phase is withdrawn after decantation. The organic phase which is washed twice with 100 ml of water at 95° C. is then dried by heating under reduced pressure. The volatile materials present are removed by molecular distillation at 120° C., yielding a colorless oil having an end temperature of liquefaction lower than −10° C., an index of refraction at 30° C. of 1.45399, a molecular weight determined by the method of lowering the vapor pressure of 1420 and a viscosity at 30° C. of 1.2 poises.

EXAMPLE 8

Preparation of a mixture of compounds of general formula I wherein A represents hydrogen, R represents 2-ethyl hexyl, R' represents a mixture of undecyl, dodecyl, tridecyl and tetradecyl; X is oxygen, Y is —CH$_2$— and n=5.

To 10.4 g (0.08 mole) of 2-ethyl hexanol there is added 0.56 ml of BF$_3$/acetic acid complex containing 33% BF$_3$. The resulting mixture is heated to 75° C. and then there are added dropwise in 35 minutes 103 g (0.40 moles) of a mixture of C$_{15}$ to C$_{18}$ fatty epoxides sold under the name Nedox 1518, the temperature being maintained at 75° C.±5° C. The reaction mass is then heated for 1 hour at 80° C. That all the epoxide introduced has indeed reacted is then verified by dosage.

To the reaction mass, with agitation, there are added 100 ml of water at 90° C. containing 4.1 g of a NaOH solution (1.2 meq/g). The aqueous phase is separated after decantation. The organic phase is washed again with 100 ml of water at 90° C.

The product is dried by heating under reduced pressure and the volatile materials present are eliminated by molecular distillation at 125° C. under 10$^{-3}$ mm Hg, yielding a pale yellow product solid at ambient temperature and liquid and clear at 30° C., having an index of refraction at 35.5° C. of 1.45947 and a molecular weight, determined by the method of lowering the vapor pressure of 1500.

EXAMPLE 9

Preparation of a mixture of compounds of general formula I wherein A represents hydrogen, R represents pentadecyl, R' is 2-ethyl hexyl, X is

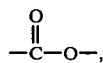

Y is oxygen and n=2.

(a) Preparation of an intermediate with n=1 as in Example 1.

(b) To 95.2 g (0.2 mole) of the intermediate compound obtained in step (a), there is added 0.3 ml of BF$_3$/acetic acid complex containing 33% BF$_3$. The resulting mixture is heated to 75° C. and then there are added dropwise 37.2 g (0.2 mole) of 2-ethyl hexyl glycidyl ether in ½ hour while maintaining the temperature at 75° C.±5° C. At the end of the addition, the temperature is maintained at 80° C. for 45 minutes. The disappearance of the epoxide introduced is verified by dosage.

To the reaction mixture there are added, with agitation, 150 ml of water at 70° C. containing 1.3 g of a 48% NaOH solution and 20 ml of isopropanol to improve decantation. The aqueous phase is separated and the organic phase is washed twice with 150 ml of water at 70° C.

The product is dried by heating under reduced pressure, and the volatile products are removed by molecular distillation at 120° C. under 10$^{-3}$ mm Hg, yielding a colorless oil having an end temperature of liquefaction of 3°–4° C., an index of refraction at 30° C. of 1.45160 and a viscosity of 30° C. of 0.45 poise.

EXAMPLE 10

Preparation of a mixture of compounds of general formula I wherein A represents hydrogen, R represents a mixture of hexadecyl and octadecyl, R' is 2-ethyl hexyl, X and Y each represent oxygen and n=2.

To 53.2 g (0.2 mole) of a mixture of cetyl and stearyl alcohols, there is added 0.3 ml of BF$_3$/acetic acid complex having 33% BF$_3$. The resulting mixture is then heated to 75° C. and there are added dropwise 74.4 g (0.4 mole) of 2-ethyl hexyl glycidyl ether. At the end of the addition the reaction mass is heated again for 1 hour at 80°–85° C. That all the epoxide introduced has reacted is verified by dosage.

To the reaction mixture, with agitation, there are added 150 ml of water at 95° C. containing 1 g of a 48% NaOH solution. The aqueous phase is separated after decantation and the oganic phase is washed 3 times with 150 ml of water at 95° C.

The product is then dried by heating under reduced pressure and the volatile products are removed by molecular distillation at 125° C. under 10$^{-3}$ mm Hg, yielding a colorless and odorless liquid having an end temperature of liquefaction of +5° C., an index of refraction at 30° C. of 1.45107 and a viscosity at 30° C. of 0.40 poise.

EXAMPLE 11

Preparation of a mixture of compounds of general formula I wherein A is hydrogen, R represents a mixture of cetyl and stearyl, R' is tert-butyl, X and Y are both oxygen and n=8.

To 63.8 g (0.25 mole) of a mixture of cetyl and stearyl alcohols there are added 1.6 ml of BF$_3$/acetic acid complex containing 33% BF$_3$. The resulting mixture is heated to 75° C. and there are then introduced dropwise in 3 hours 260 g (2 moles) of tertiobutyl glycidyl ether while maintaining the temperature at 75° C.±5° C. At the end of the addition, the reaction mass is heated to 80° C. for 1 hour. The disappearance of the epoxide introduced is verified by dosage.

The product obtained is then washed twice with 100 ml of water at 90° C., dried by heating under reduced pressure and filtered, yielding a colorless oil which solidifies at 0° C. and has an index of refraction at 30° C. of 1.44480 and a viscosity at 30° C. of 4.16 poises.

EXAMPLE 12

Preparation of a mixture of compounds of general formula I wherein A represents hydrogen, R represents 2-ethyl hexyl, R' is isopropyl, X and Y are both oxygen and n=8.

To 15.6 g (0.12 mole) of 2-ethyl hexanol there is added 1 ml of BF$_3$/acetic acid complex containing 33% BF$_3$. The resulting mixture is heated to 75° C. and there are added dropwise in 1 hour 114 g (0.96 mole) of isopropyl glycidyl ether while maintaining the temperature at 75° C.±5° C. After the addition, the reaction mass is again heated for 2 hours at 80° C., and the acidity due to the catalyst is neutralized with 2.5 g of sodium methylate in methanol (5.49 meq/g). The reaction mixture is washed three times with 200 ml of water at 95° C.

The product is then dried by heating under reduced pressure and the volatile compounds are removed by molecular distillation at 120° C., yielding a colorless oil having an end temperature of liquefaction lower than −10° C., an index of refraction at 30° C. of 1.44208, a viscosity at 30° C. of 1.35 poises and a molecular weight, determined by the method of lowering the vapor pressure, of 1010.

EXAMPLE 13

Preparation of a mixture of compounds of general formula I wherein A represents hydrogen, R represents the hydrocarbon residue of isostearic acid, R' represents 2-ethyl hexyl, X is

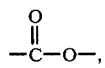

Y is oxygen and n=2.5.

To 63.7 g (0.2 mole) of isostearic acid there is added 0.33 g (0.006 mole) of sodium methylate. The resulting mixture is heated to 130° C. under a nitrogen atmosphere. There are then added dropwise in 15 minutes 37.2 g (0.2 mole) of 2-ethyl hexyl glycidyl ether.

After 6 hours of heating at 130° C., the amount of the reaction determined by acid index is 93%. The catalyst is then neutralized with 0.5 ml of concentrated HCl (d=1.19).

To 79 g (0.16 mole) of the product thus obtained, there is added 0.6 ml of BF$_3$/acetic acid complex containing 33% BF$_3$. The mixture is heated to 75° C. and there are added dropwise in 25 minutes 44.6 g (0.24 mole) of 2-ethyl hexyl glycidyl ether while maintaining the temperature at 75° C.±5° C. The mixture is then heated for 1 hour at 80° C.

To the reaction mixture there are added, with agitation, 100 ml of water at 95° C., containing 1.7 g of a 48% NaOH solution and 23 ml of isopropanol to facilitate decantation. The aqueous phase is withdrawn and the organic phase is washed twice with 100 ml of water at 95° C.

The product is dried by heating under reduced pressure and the volatile compounds are removed by molecular distillation at 122° C., yielding a golden yellow oil having an end temperature of liquefaction lower than −10° C., an index of refraction at 30° C. of 1.45431, a viscosity at 30° C. of 0.68 poise and a molecular weight, determined by the method of lowering the vapor pressure, of 1035.

EXAMPLE 14

Preparation of a mixture of compounds of general formula I wherein R represents the hydrocarbon residue of a branched alcohol sold under the name of Sidopol 16, R' represents the hydrocarbon residue of isostearic acid, A represents a mixture of hydrogen and

wherein R' has the meaning given immediately above, X is oxygen, Y is

and n=5.

Step (a): To 60 g (0.2 mole) of Sidopol 16 there is added 0.7 ml of BF$_3$/acetic acid complex. The resulting mixture is heated to 70° C. and there are added dropwise 130 g (1 mole) of tertio-butyl glycidyl ether in 2 hours.

The disappearance of the epoxide introduced is verified by dosage. The acidity of the catalyst is neutralized with 0.6 g of a 48% solution of NaOH. The product is then washed three times with 150 ml of water at 95° C. and dehydrated by heating under reduced pressure.

Step (b): To 31 g (0.035 mole) of the compound obtained in step (a) there are added 0.8 g of p-toluene sulfonic acid and then 52 g (0.163 mole) of isostearic acid. The resulting mixture is heated under a nitrogen atmosphere to 100°-115° C.

During the course of the heating an evolution of isobutylene gases is observed.

After 3¾ hours of heating the amount of reaction is close to 100% as determined by the acid index.

To the reaction mass there are introduced, with agitation, 100 ml of water at 95° C. containing 2.25 g of a 48% NaOH solution and 20 ml of isopropanol to facilitate decantation. The aqueous phase is separated and the organic phase is washed twice with 100 ml of water at 95° C.

The product is dried by heating under reduced pressure, yielding a brown oil which solidifies on cooling to a temperature approaching −15° C. The product has an index of refraction at 30° C. of 1.46235, a molecular weight determined by the method of lowering the vapor pressure of 1630 and a viscosity at 30° C.=1.89 poises.

EXAMPLE 15

Preparation of a mixture of compounds of general formula I wherein R represents the hydrocarbon residue of a branched alcohol sold under the name of Sidopol 16, R' represents the hydrocarbon residue of lauric acid, A represents a mixture of hydrogen and

wherein R' has the meaning given immediately above, X is oxygen, Y is

and n=5.

Step (a): Preparation of an intermediate compound as set forth in step (a) of Example 14.

Step (b): To 38 g (0.04 mole) of the compound obtained in step (a), there are added 0.8 g of sulfoacetic acid and 40.4 g (0.2 mole) of lauric acid. The mixture is heated to 100°-110° C. under a nitrogen atmosphere.

After 3 hours of heating the amount of the reaction determined by acid index is 96%.

To the reaction mixture there are added, with agitation, 200 ml of water at 95° C. containing 1.2 g of a 48% NaOH solution and 30 ml of isopropanol to facilitate decantation. The aqueous phase is separated and the organic phase is washed once with 150 ml of water at 95° C.

The product is dried by heating under reduced pressure, yielding a yellow oil having an end temperature of liquefaction of +5° C., an index of refraction at 30° C. of 1.45779 and a viscosity at 30° C. of 1.39 poises.

EXAMPLE 16

Preparation of a mixture of compounds of general formula I wherein R represents a mixture of alkyl radicals containing 11 to 15 carbon atoms derived from an alcohol sold under the name Dobanol 25, R' represents the hydrocarbon residue of 2-ethyl hexanoic acid, A represents a mixture of hydrogen and

wherein R' has the meaning given immediately above, X is oxygen, Y is

and n=4.

(a) To 31 g (0.15 mole) of Dobanol 25 there is added 0.35 ml of BF₃/acetic acid complex. The mixture is heated to 75° C. and there are added dropwise in 1 hour 78 g (0.6 mole) of tertiobutyl glycidyl ether while maintaining the temperature at 75° C.±5° C.

At the end of the addition, the reaction mass is heated to 80° C. for 1½ hours. That all the epoxide introduced has been reacted is verified by dosage.

To the reaction mass there are added, with agitation, 150 ml of water at 90° C. containing 0.7 g of a 48% solution of NaOH. The aqueous phase is separated after decantation and the organic phase is washed 3 times with 150 ml of water at 90°–95° C.

The product is dried by heating under reduced pressure and then filtered on fritted glass.

(b) To 43.5 g (0.06 mole) of the product obtained in step (a) there are added 35.2 g (0.24 mole) of 2-ethyl hexanoic acid and 1.6 g of p-toluene sulfonic acid. The mixture is heated under a nitrogen atmosphere to 110°–120° C. for 7 hours. The amount of the reaction, determined by dosage of the remaining acid, is 95%.

To the reaction mixture there are added, with agitation, 100 ml of water at 90° C. containing 1.5 g of a 48% NaOH solution to neutralize the acid which has not reacted. The aqueous phase is separated after decantation and the organic phase is washed twice with 100 ml of water at 90° C.

The product is dried by heating under reduced pressure, yielding an amber colored oil having an end temperature of liquefaction lower than −15° C., an index of refraction at 30° C. of 1.45531 and a viscosity at 30° C. of 1.58 poises.

EXAMPLE 17

Preparation of a mixture of compounds of general formula I wherein R represents a mixture of hexadecyl and octadecyl, R' represents the hydrocarbon residue of 2-ethyl hexanoic acid, A represents a mixture of hydrogen and

wherein R' has the meaning given immediately above, X is oxygen, Y is

and n=6.

(a) To 26.6 g (0.1 mole) of a mixture of cetyl and stearyl alcohols there is added 0.35 ml of BF₃/acetic acid complex. The mixture is heated to 70° C. and there are added in 1 hour 15.78 g (0.6 mole) of tertiobutyl glycidyl ether while maintaining the temperature at 70° C.±5° C.

At the end of the addition, the reaction mass is heated again for 1½ hours at 80° C. That the epoxide introduced has disappeared is vertified by dosage.

To the reaction mixture there are added, with agitation, 150 ml of water at 95° C. containing 0.5 g of a 48% NaOH solution. The aqueous phase is separated after decantation and the organic phase is washed twice with 150 ml of water at 95° C.

The product is dried by heating under reduced pressure.

(b) To 95 g (0.09 mole) of the compound obtained in step (a) there are added 80 g (0.54 mole) of 2-ethyl hexanoic acid and 1.8 g of sulfoacetic acid. The mixture is heated under a nitrogen atmosphere to 100°–135° C. During the course of the heating a significant evolution of gases is observed.

After 7 hours of heating the amount of the reaction, determined by dosage of the remaining acidity, is 86%.

To the reaction mass there are added, with agitation, 200 ml of water at 95° C. containing 7 g of a 48% NaOH solution to neutralize the remaining acidity. After decantation the aqueous phase is separated and the organic phase is washed twice with 200 ml of water at 95° C.

The product is dried by heating under reduced pressure, yielding a brown oil which solidifies at about −15° C. and has an index of refraction at 30° C. of 1.45774 and a viscosity at 30° C. of 2.78 poises.

EXAMPLE 18

Preparation of a mixture of compounds of general formula I wherein R represents a mixture of alkyl radicals containing from 11 to 15 carbon atoms, derived from an alcohol sold under the name of Dobanol 25, R' represents the hydrocarbon residue of lauric acid, A represents a mixture of hydrogen and

wherein R' has the meaning given immediately above, X is oxygen, Y is

and n=4.

(a) Preparation of an intermediate compound as set forth in step (a) of Example 16.

(b) To 43.5 g (0.06 mole) of the intermediate compound of step (a) there are added 48.5 g (0.24 mole) of lauric acid and 0.9 g of sulfoacetic acid. The mixture is heated to 105° C. under a nitrogen atmosphere. After 6 hours of heating the amount of reaction determined by dosage of the remaining acidity is close to 100%.

To the reaction mass there are added, with agitation, 150 ml of water at 95° C. containing 0.5 g of a 48% NaOH solution. The aqueous phase is separated after decantation and the organic phase is washed twice with 150 ml of water at 95° C.

The product is dried by heating under reduced pressure, yielding a yellow oil having an end temperature of liquefaction of +18° C., an index of refraction at 30° C.

of 1.45748, a viscosity at 30° C. of 1.12 poises and a molecular weight determined by the method of lowering the vapor pressure of 1090.

EXAMPLE 19

Preparation of a mixture of compounds of general formula I wherein A represents hydrogen, R represents 2-ethyl hexyl, R' is tert-butyl, X and Y are both oxygen and n=8.

To 40.5 g of 2-ethyl hexanol (0.31 mole) there are added 1.4 ml of $BF_3$/acetic acid complex. The mixture is heated to 75° C. and there are added dropwise in 4 hours 325 g (2.5 moles) of tertiobutyl glycidyl ether while maintaining the temperature at 75° C.±5° C. At the end of the addition, the reaction mass is heated again for 2 hours at 80° C.

Under reduced pressure the small amount of unreacted epoxide (1.2%) is removed and the reaction mass is washed twice with 300 ml of water at 90° C.

The product is then dried by heating under reduced pressure, yielding a colorless oil which solidifies at −15° C. and has an index of refraction at 30° C. of 1.44280, a molecular weight determined by the method of lowering the vapor pressure of 970 and a viscosity at 30° C.=8.21 poises.

EXAMPLE 20

Preparation of a mixture of compounds of general formula I wherein A represents hydrogen, R represents $C_{12}H_{25}$, R' is a mixture of alkyl radicals containing 11 to 14 carbon atoms, X is oxygen, Y is —$CH_2$— and n=5.

To 13 g (0.07 mole) of molten lauric acid there is added 0.4 ml of $BF_3$/acetic acid complex. The mixture is heated to 75° C. and there are added dropwise 88.5 g (0.35 mole) of a mixture of $C_{15}$ to $C_{18}$ fatty epoxides sold under the name Nedox 1518, while maintaining the temperature at 75° C.±5° C. At the end of the addition, the reaction mass is heated again for ½ hour at 80° C. The disappearance of the epoxide introduced is verified by dosage.

To the molten reaction mixture there are added, with agitation, 200 ml of water at 95° C. containing 1 g of a 48% NaOH solution. After decantation the aqueous phase is separated and the organic phase is washed twice with 200 ml of water at 95° C.

The product is dried by heating under reduced pressure, yielding after cooling a slightly yellow wax having an end temperature of liquefaction of 53° C.

EXAMPLE 22

Preparation of a mixture of compounds of general formula I wherein A represents hydrogen, R represents a mixture of $C_{16}H_{33}$ and $C_{18}H_{37}$, R' represents the hydrocarbon residue of isostearyl alcohol, X and Y are both oxygen and n=5.

To 9.6 g (0.036 mole) of a mixture of cetyl and stearyl alcohols, there is added 0.30 ml of $BF_3$/acetic acid complex. The mixture is heated to 75° C. and there are added dropwise 62 g (0.18 mole) of isostearyl glycidyl ether, while maintaining the temperature at 75° C.±5° C. At the end of the addition, the reaction mass is heated again for ½ hour at 80° C.

The disappearance of the epoxide introduced is verified by dosage. To the reaction mixture there are added, with agitation, 70 ml of water at 90° C. containing 3.3 g of NaOH (1.2 meq/g). After decantation the aqueous phase is separated and the organic phase is washed again twice with 70 ml of water at 80° C.

The product is dried by heating under reduced pressure and then filtered. The volatile products are removed by molecular distillation at 125° C., yielding a colorless, slightly cloudy oil having an end temperature of liquefaction of 12° C., an index of refraction at 30° C. of 1.46050, a viscosity at 30° C. of 1.4 poises and a molecular weight determined by the method of lowering the vapor pressure of 1425.

EXAMPLE 23

Preparation of a mixture of compounds of formula I wherein R represents a mixture of $C_{16}H_{33}$ and $C_{18}H_{37}$, R' represents the hydrocarbon residue of 2-ethyl hexanoic acid, A represents a mixture of hydrogen and

wherein R' has the meaning given immediately above, X is oxygen, Y is

and n=2.

(a) There is prepared in accordance with French Pat. No. 1,477,048 a mixture of polyhydroxylated polyethers represented by the formula

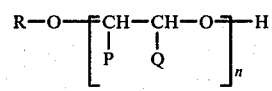

wherein R represents a mixture of $C_{16}H_{33}$ and $C_{18}H_{37}$, one of P and Q represents hydrogen and the other represents —$CH_2OH$ and n=2.

(b) To 104 g of the above mixture (0.25 mole) there are added 118 g of 2-ethyl hexanoic acid (0.82 mole), 2 ml of phosphoric acid and 75 g of xylene. The reaction mixture is heated to reflux thus eliminating the water formed until the amount of reaction determined by acid index is at least 95%.

The catalyst and the remaining acid are neutralized with sodium carbonate and the reaction mass is then filtered and the xylene is removed by distillation under reduced pressure. The product is then washed with 100 ml of water and dried by heating under reduced pressure, yielding a light yellow oil having an end temperature of liquefaction of 14° C.

EXAMPLE 24

Preparation of a mixture of compounds of general formula I wherein R represents the hydrocarbon residue of lanolic acid, R' is $C_8H_{17}$, X is

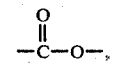

Y is —$CH_2$—, A represents hydrogen and n=3.

To 167 g of molten lanolic acid (0.4 mole) there are added 1.1 g of powdered sodium methylate (20 meq). The temperature of the mixture is then raised to 130° C. under a nitrogen atmosphere and there are added dropwise in 30 minutes 73.6 g (0.4 mole) of 1,2-epoxydodecane. The temperature of the mixture is then maintained at 130° C. for 6 hours. The amount of the reaction obtained under these conditions, determined by measuring the free acidity is 93%.

The product thus obtained is washed by agitation with 225 ml of water at 90° C. containing NaOH in an amount necessary for the neutralization of residual acidity and in the presence of 100 ml of isopropanol. The organic phase recovered after decantation is again washed twice with 225 ml of water at 90° C. then dehydrated at 100° C. under reduced pressure, yielding a brown wax having a drop point of 45° C.

To 60.2 g (0.1 mole) of the product obtained above there is added 0.5 ml of $BF_3$/ether complex. The temperature of the mixture is raised to 75° C. and there are added 36.8 g (0.2 mole) of 1,2-epoxydodecane in 45 minutes, while maintaining the temperature at 75±5° C.

The mixture is then heated for 30 minutes at 75° C. and a check is made, by the determination of the epoxide index, that there does not remain in the medium any oxirane groups.

The product thus obtained is washed, with agitation, with 100 ml of water at 90° C. containing an amount of NaOH necessary for the neutralization of the acidity due to the catalyst and in the presence of 30 ml of isopropanol to improve decantation.

The organic phase recovered after decantation is washed again twice with 100 ml of water at 90° C., then dehydrated under reduced pressure at 90° C., yielding slightly thick, light brown paste having a drop point of 32.5° C.

EXAMPLE 25

Preparation of a mixture of compounds of general formula I wherein R—$C_{16}H_{33}$, R' is a mixture of $C_{12}H_{25}$ and $C_{14}H_{29}$, X and Y are both oxygen, A is hydrogen and n=8.

To 36.3 g (0.15 mole) of molten $C_{16}$ fatty alcohol sold under the name Alfol 16 RD, there are added 1.6 ml of $BF_3$/acetic acid complex. There are then added dropwise in 2 hours 25 minutes 353 g of an alkyl glycidyl ether sold under the name of Epoxyde 8, while maintaining the temperature at 65° C.±3° C.

There is then checked by a determination of the epoxide latex, that all the epoxide added has reacted.

There is thus obtained a product which is liquid at ambient temperature, slightly yellow and which has an end melting point of 16° C. Further, the product has a molecular weight in toluene, determined by the method of lowering the vapor pressure of 1210 and a hydroxyl index of 0.58–0.56 meq/g.

EXAMPLE 26

Preparation of a mixture of compounds of formula I wherein R represents a mixture of $C_{16}H_{33}$ and $C_{18}H_{37}$, R' represents a mixture of $C_{10}H_{21}$ and $C_{12}H_{25}$, X is oxygen, Y is —$CH_2$—, A is hydrogen and n=5.

To 21.3 g (0.08 meq) of a 50:50 molten mixture of cetyl and stearyl alcohols there is added 0.6 ml of $BF_3$/acetic acid complex. To this mixture there are added dropwise in 1 hour 40 minutes, 100 g (0.4 mole) of a mixture of $C_{14}$ and $C_{16}$ α-epoxides sold under the name of α-Olefin Oxide 16, while maintaining the temperature at 68° C.±2° C. After the addition the temperature is maintained at 68° for 3 hours.

After verification of the complete disappearance of free epoxide by determining the epoxide index, the product obtained is washed, with agitation, with 100 ml of boiling water containing an amount of NaOH necessary for the neutralization of the acidity due to the catalyst. The organic phase recovered after decantation is again washed twice with 100 ml of water at 90° C. and then dehydrated under reduced pressure.

After removal of volatile impurities by molecular distillation at 130° C., there is obtained a product which is a white solid at temperatures lower than 30° C. and which is a colorless liquid above said temperature.

The product has a molecular weight, determined in toluene by the method of lowering the vapor pressure of 1170 and a hydroxyl index of 1.00–1.02 meq/g.

EXAMPLE 27

Preparation of a mixture of compounds of general formula I wherein R represents the hydrocarbon residue of lanolin alcohol, R' represents a mixture of $C_{10}H_{21}$ and $C_{12}H_{25}$, X is oxygen, Y is —$CH_2$—, A is hydrogen and n=3.

To 80 g (0.2 mole) of lanolin alcohol sold under the name Satulan, previously dehydrated by agitation under reduced pressure, there are added 1.2 ml of $BF_3$/ether complex. The temperature of the resulting mixture is then raised to 80° C. and there are added dropwise 143 g (0.6 mole) of a mixture of $C_{14}$ and $C_{16}$ epoxides sold under the name of α-Olefin Oxide 16. The temperature of the mixture is then maintained at 80° C. for 2 hours so that all the epoxide added is consumed.

The product thus obtained is washed with agitatin with 175 ml of water at 90° C. containing the amount of NaOH necessary to neutralize the acidity due to the catalyst. The organic phase, separated after decantation, is again washed twice with 175 ml of water at 90° C. then dehydrated under reduced pressure.

After removal of volatile impurities by molecular distillation at 150° C. under $10^{-3}$ mm Hg, there is obtained a pale yellow waxy looking product having a drop point of 37° C. and an end melting point of 31°–32° C.

EXAMPLE 28

Preparation of a mixture of compounds of general formula I wherein R represents the hydrocarbon residue of lanolin alcohol, R' represents a mixture of $C_{10}H_{21}$ and $C_{12}H_{25}$, X is oxygen, Y is —$CH_2$—, A is hydrogen and n=5.

To 48 g (0.12 mole) of lanolin alcohol sold under the name of Satulan, previously dehydrated under reduced pressure, there are added 1.1 ml of $BF_3$/acetic acid complex. The temperature of the resulting mixture is raised to 80° C. and there are then added in 2½ hours 143 g (016 mole) of a mixture of $C_{14}$ and $C_{16}$ α-epoxides sold under the name of α-Olefin Oxide 16. After the addition, the temperature is maintained at 80° C. for 1 hour and a check is made by determining the epoxide index that there no longer remains any oxirane groups.

The product thus obtained is washed, neutralized and purified in accordance with the procedures set forth in Example 27. The said product is a pale yellow wax having a soft consistency, an end melting point of 27°–28° C. and a drop point of 30.5° C.

EXAMPLE 29

Preparation of a mixture of compounds of general formula I wherein R represents the hydrocarbon residue of lanolin alcohol, R' represents a mixture of $C_{10}H_{21}$ and $C_{12}H_{25}$, X is oxygen, Y is —$CH_2$—, A is hydrogen and n=1.5.

To 80 g of lanolin alcohol sold uner the name of Satulan, previously dehydrated at 90° C. under reduced pressure, there is added 0.6 ml of $BF_3$/ether complex. The temperature of the resulting mixture is raised to 80° C. and there are added dropwise in 35 minutes 71.4 g (0.3 mole) of a mixture of $C_{14}$ and $C_{16}$ α-epoxides sold under the name of α-Olefin Oxide 16 while maintaining the temperature at 80° C.±5° C. At the end of the addition, the mixture is again heated for 1 hour at this temperature. Then, by determining the epoxide index, it is verified that there does not remain any oxirane groups in the medium.

The product thus obtained is dissolved in 80 ml of isopropanol and washed with agitation with 250 ml of water at 90° C. containing the amount of NaOH necessary for the neutralization of the acidity due to the catalyst.

The organic phase recovered after decantation is washed again under the same conditions with 250 ml of water at 90° C. and then dehydrated under reduced pressure.

The volatile impurities are removed by molecular distillation at 150° C. under $10^{-3}$ mm Hg, yielding a light yellow paste having an end melting point of 45° C., a drop point of 46°–48° C. and a hydroxyl index of 1.41 meq/g.

EXAMPLES OF COSMETIC COMPOSITIONS

In the following cosmetic compositions, those which are aerosols are prepared in accordance with conventional methods.

For those cosmetic compositions containing water, the method of preparation is as follows: (1) heat to about 80° C. the oily phase (emulsifying agents, couplers, oils); (2) heat to the same temperature the demineralized water containing a preservative and neutralized Carbopol, if the composition contains it; (3) make the emulsion and (4) cool with agitation up to ambient temperature. Carbopol 934, 940 and 941 are commercial carboxy vinyl polymers.

EXAMPLE 30

| Milk for the hands | |
| --- | --- |
| Stearic acid | 5.0 g |
| Triethanolamine | 2.5 g |
| Cetyl alcohol | 1.0 g |
| Product of Example 10 | 12.0 g |
| Methyl parahydroxy benzoate | 0.3 g |
| Sterile demineralized water | 79.2 g |
| | 100 g |

EXAMPLE 31

| Day Cream for oily skin | |
| --- | --- |
| Stearyl ether polyoxyethylenated with 10 moles of ethylene oxide | 1.3 g |
| Cetyl ether polyoxyethylenated with 10 moles of ethylene oxide | 1.3 g |
| Cetyl alcohol | 1.0 g |
| Product of Example 9 | 20.0 g |
| Carbopol 934 | 0.3 g |
| Triethanolamine | 0.3 g |
| Methyl parahydroxy benzoate | 0.3 g |
| Sterile demineralized water | 75.5 g |
| | 100 g |

EXAMPLE 32

| Day cream for dry skin | |
| --- | --- |
| Stearyl ether polyoxyethylenated with 10 moles of ethylene oxide | 1.3 g |
| Cetyl ether polyoxyethylenated with 10 moles of ethylene oxide | 1.3 g |
| Cetyl alcohol | 1.0 g |
| Product of Example 1 | 20.0 g |
| Carbopol 934 | 0.3 g |
| Triethanolamine | 0.3 g |
| Methyl parahydroxy benzoate | 0.3 g |
| Sterile demineralized water | 75.5 g |
| | 100.0 g |

EXAMPLE 33

| Day cream for dry skin | |
| --- | --- |
| Stearyl ether polyoxyethylenated with 10 moles of ethylene oxide | 1.3 g |
| Cetyl ether polyoxyethylenated with 10 moles of ethylene oxide | 1.3 g |
| Product of Example 7 | 20.0 g |
| Carbopol 934 | 0.3 g |
| Triethanolamine | 0.3 g |
| Cetyl alcohol | 1 g |
| Methyl parahydroxy benzoate | 0.3 g |
| Sterile demineralized water | 75.5 g |
| | 100.0 g |

EXAMPLE 34

| Body milk | |
| --- | --- |
| Stearic acid | 3.0 g |
| Triethanolamine | 1.7 g |
| Product of Example 3 | 10.0 g |
| Hexadecyl alcohol | 1.5 g |
| Carbopol 940 | 0.2 g |
| Methyl parahydroxy benzoate | 0.3 g |
| Sterile demineralized water | 83.3 g |
| | 100.0 g |

A similarly effective body milk is prepared by replacing the product of Example 3 by the same quantity of the product of Example 4.

EXAMPLE 35

| Night cream for dry skin | |
| --- | --- |
| Sorbitan monostearate polyoxyethylenated with 20 moles of ethylene oxide | 3.0 g |
| Glycerol monostearate, self-emulsifying | 2.0 g |
| Cetyl alcohol | 2.0 g |
| Product of Example 5 | 40.0 g |
| Stearic acid | 2.0 g |
| Methyl parahydroxy benzoate | 0.3 g |
| Sterile demineralized water | 50.7 g |
| | 100.0 g |

EXAMPLE 36

| Night cream for oily skin | |
| --- | --- |
| Sorbitan monostearate polyoxyethylenated with 20 moles of ethylene oxide | 3.0 g |

-continued

| Night cream for oily skin | |
|---|---|
| Glycerol monostearate, self-emulsifying | 2.0 g |
| Cetyl alcohol | 2.0 g |
| Product of Example 13 | 40.0 g |
| Stearic acid | 2.0 g |
| Methyl parahydroxy benzoate | 0.3 g |
| Sterile demineralized water | 50.7 g |
| | 100.0 g |

EXAMPLE 37

| Makeup remover cream | |
|---|---|
| Stearic acid | 3.0 g |
| Cetyl alcohol | 3.0 g |
| Glycerol monostearate, self-emulsifying | 6.0 g |
| Product of Example 6 | 10.0 g |
| Petrolatum oil | 20.0 g |
| Propylene glycol | 2.5 g |
| Triethanolamine | 1.0 g |
| Methyl parahydroxy benzoate | 0.3 g |
| Sterile demineralized water | 54.2 g |
| | 100.0 g |

EXAMPLE 38

| Skin care cream | |
|---|---|
| Stearic acid | 15.0 g |
| Beeswax | 3.0 g |
| Lanolin | 2.0 g |
| Polyethyleneglycol stearate (with 50 moles of ethyleneglycol) | 5.0 g |
| Sorbitol | 10.0 g |
| Product of Example 8 | 10.0 g |
| Petrolatum oil | 25.0 g |
| Isopropyl palmitate | 5.0 g |
| Methyl parahydroxy benzoate | 0.3 g |
| Sterile demineralized water | 24.7 g |
| | 100.0 g |

EXAMPLE 39

| Dry antiperspirant spray | |
|---|---|
| Aluminum chlorhydrate | 3.5 g |
| Colloidal silica | 0.3 g |
| Perfume | 0.7 g |
| Product of Example 11 | 5.5 g |
| Propellants-Freon 11 (trichloromonofluoromethane) and Freon 12, (dichlorodifluoromethane) 61.5/38.5, q.s.p. | 100.0 g |

EXAMPLE 40

| Dry antiperspirant spray | |
|---|---|
| Aluminum chlorhydrate | 3.5 g |
| Talc | 0.3 g |
| Perfume | 0.4 g |
| Product of Example 11 | 2.0 g |
| Propellant-Freon 11 and Freon 12 (61.5/38.5) q.s.p. | 100.0 g |

EXAMPLE 41

| Personal hygiene spray | |
|---|---|
| Product of Example 19 | 0.2 g |
| Hexylene glycol | 0.1 g |
| Hexadecyl alcohol | 0.05 g |
| Caprylate of $C_{12}$-$C_{18}$ fatty | 0.1 g |
| Vitamins, A, $D_3$ and E | 0.01 g |
| Perfume | 0.15 g |
| Propellants, Freon 11 and Freon 12, (61.5/38.5), q.s.p. | 100.0 g |

EXAMPLE 42

| Lip rouge | |
|---|---|
| Ozokerite | 13 g |
| Ricin oil | 35 g |
| Hydrogenated lanolin | 5 g |
| Hydrogenated palm oil | 5 g |
| Oleyl alcohol | 5 g |
| Product of Example 13 | 21.75 g |
| Isopropyl lanolate | 10 g |
| Liquid lanolin | 5 g |
| B.H.T. (2,6-di-tert-butyl-p-cresol) | 0.1 g |
| Methyl parahydroxy benzoate, q.s.p. | 100.0 g |
| In addition: | |
| Dyes | |
| Titanium oxide | sufficient for |
| Nacreous agent | tint desired |

EXAMPLE 43

| Fluid dye foundation | |
|---|---|
| Stearic acid | 4.6 g |
| Petrolatum oil | 5 g |
| Cetyl alcohol | 0.5 g |
| Product of Example 10 | 18 g |
| Triethanolamine | 1.8 g |
| Bentonite | 2 g |
| Methyl parahydroxy benzoate | 0.3 g |
| Demineralized water, q.s.p. | 100 g |
| In addition: | |
| Titanium oxide | |
| Kaolin | sufficient for |
| Iron Oxide | tint desired |

EXAMPLE 44

| Cream dye foundation | |
|---|---|
| Beeswax | 9 g |
| Cetyl alcohol | 1 g |
| Diethanolamine cetyl phosphate | 0.5 g |
| Petrolatum oil | 10 g |
| Product of Example 9 | 18 g |
| Borax | 0.8 g |
| Methyl parahydroxy benzoate | 0.3 g |
| Demineralized water, q.s.p. | 100 g |
| In addtion: | |
| Titanium oxide | |
| Kaolin | sufficient for |
| Iron oxides | tint desired |

EXAMPLE 45

| Cheek rouge | |
|---|---|
| Isopropyl stearate | 29 g |
| Product of Example 2 | 34 g |

| Cheek rouge | |
|---|---|
| Glycerol monostearate | 30 g |
| Kaolin | 2 g |
| Titanium dioxide | 3.5 g |
| Iron oxide | 1.5 g |
| | 100 g |

EXAMPLE 46

| Product for imparting a shiny appearance to hair in the form of a spray | |
|---|---|
| Composition of the active component | |
| Product of Example 19 | 47 g |
| Silicone oil | 14.5 g |
| Petrolatum oil | 5 g |
| Ethyl alcohol, q.s.p. | 100 g |
| Aerosol composition | |
| Active component | 15 g |
| Freon 11/Freon 12 (61.5/38.5) | 85 g |

EXAMPLE 47

| Product for imparting a shiny appearance to the hair in the form of a spray | |
|---|---|
| Composition of the active component | |
| Product of Example 12 | 15.5 g |
| Propylene glycol | 31 g |
| Petrolatum oil | 6.5 g |
| Silicone oil | 13.5 g |
| Perfume | 0.3 g |
| Ethyl alcohol, q.s.p. | 100 g |
| Aerosol composition | |
| Active component | 15 g |
| Freon 11/Freon 12 (61.5/38.5) | 85 g |

EXAMPLE 48

| Skin care cream | |
|---|---|
| Sorbitan monostearate polyoxyethylenated with 20 moles of ethylene oxide | 3.0 g |
| Cetyl alcohol | 1.0 g |
| Petrolatum oil | 30.0 g |
| Product of Example 20 | 17.0 g |
| Methyl parahydroxy benzoate | 0.3 g |
| Demineralized water, q.s.p. | 100 g |

EXAMPLE 49

| Night cream for dry skin | |
|---|---|
| Cetyl ether polyoxyethylenated with 10 moles of ethylene oxide | 4.0 g |
| Cetyl alcohol | 2.0 g |
| Petrolatum oil | 12 g |
| Isopropyl palmitate | 5 g |
| Product of Example 22 | 5 g |
| Methyl parahydroxy benzoate | 0.3 g |
| Demineralized water, q.s.p. | 100 g |

EXAMPLE 50

| Night cream for very dry skin | |
|---|---|
| Sorbitan monostearate polyoxyethylenated with 20 moles of ethylene oxide | 2.5 g |
| Stearyl alcohol | 2.0 g |
| Product of Example 14 | 5.0 g |
| Petrolatum oil | 30.0 g |
| Lanolin | 5.0 g |
| Carbopol 941 | 0.4 g |
| Triethanolamine | 0.4 g |
| Methyl parahydroxy benzoate | 0.3 g |
| Sterile demineralized water, q.s.p. | 100 g |

A similarly effective night cream is prepared by replacing the product of Example 14 by the same quantity of the product of Example 18.

EXAMPLE 51

| Lip rouge | |
|---|---|
| Microcrystalline wax | 10 g |
| Carnauba wax | 5 g |
| Lanolin | 17 g |
| Product of Example 29 | 10 g |
| Liquid lanolin | 18 g |
| Lanolin alcohol | 10 g |
| Mineral oil | 10 g |
| Cetyl ricinoleate | 20 g |
| BHT - antioxidant | 0.1 g |
| | 100.1 g |

EXAMPLE 52

| Lip rouge | |
|---|---|
| Carnauba wax | 3 g |
| Ozokerite | 4 g |
| Candelilla wax | 5 g |
| Beeswax | 8 g |
| Butyl stearate | 5 g |
| Mineral oil | 10 g |
| Product of Example 27 | 10 g |
| Ricin oil | 60 g |
| BHA (butylated hydroxy anisole) antioxidant | 0.1 g |
| | 100.1 g |

EXAMPLE 53

| Lip rouge | |
|---|---|
| Ozokerite | 10 g |
| Carnauba wax | 5 g |
| Candelilla wax | 8 g |
| Isopropyl lanolate | 10 g |
| Product of Example 28 | 6 g |
| Petrolatum | 16 g |
| Mineral oil | 45 g |
| BHT - antioxidant | 0.1 g |
| | 100.1 g |

To obtain a lacquered lip rouge there is added to the compositions of Examples 51-53, 8-12 percent by weight of a dye. To obtain a nacreous lip rouge there is added 4-6% of a dye plus a nacreous agent such as bismuth oxychloride-20 to 30 percent and titanium oxide-10-53%.

In both cases, a perfume is also added.

EXAMPLE 54

| Cream | |
|---|---|
| Dehymuls E* | 5 g |
| Perhydrosqualene | 24.5 g |
| Beeswax | 5 g |
| Product of Example 29 | 15 g |
| Magnesium sulfate | 0.5 g |
| Methyl parahydroxy benzoate | 0.3 g |
| Water | 49.7 g |
| | 100.0 g |

*Dehymuls E = a mixture of high molecular weight esters sold by DEHYDAG.

What is claimed is:

1. A compound in the form of an oil or wax having the formula

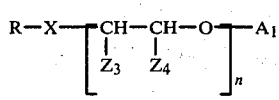

wherein

R is selected from the group consisting of alkyl having 7 to 20 carbon atoms, the hydrocarbon residue of lanolin when X is oxygen and the hydrocarbon residue of lanolic acid when X is

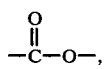

X represents a member selected from the group consisting of oxygen and carbonyloxy having the formula

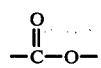

linked to R through the free bond of the carbon atom of the carbonyloxy group,
one of $Z_3$ and $Z_4$ represents hydrogen and the other represents —$CH_2$—$Y_1$—$R'_1$ wherein $Y_1$ represents a member selected from the group consisting of —$CH_2$—, oxygen and carbonyloxy of the formula

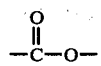

linked to $R'_1$ through the free bond of the carbon atom of the carbonyloxy group and $R'_1$ represents alkyl having from 7 to 20 carbon atoms with the proviso that $R'_1$ can have different values in the said repeating units of a given compound of said formula in (a);
$A_1$ is selected from the group consisting of hydrogen and when $Y_1$ is carbonyloxy a mixture of hydrogen and

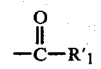

wherein $R'_1$ has the meaning given above; and
n is a whole or decimal number greater than 1 and lower than or equal to 10.

2. A mixture of compounds of claim 1.
3. The compound of claim 1 wherein at least one of R and $R'_1$ is branched chain alkyl.
4. The compound of claim 1 wherein R is the hydrocarbon residue of a R—OH alcohol selected from the group consisting of octanol, decanol, dodecanol, tetradecanol, hexadecanol, octadecanol, eicosanol, 2-ethyl hexanol, 2,2-dimethyl hexanol, 3,7-dimethyl octanol, 2-hexyl decanol, 2-octyl dodecanol, isostearyl alcohol and a mixture thereof.
5. The compound of claim 1 wherein R is the hydrocarbon residue of an oxo alcohol.
6. The compound of claim 1 wherein R is the hydrocarbon residue of lanolin alcohol.
7. The compound of claim 1 wherein R is the hydrocarbon residue of a R—COOH acid selected from the group consisting of octanoic acid, decanoic acid, dodecanoic acid, tetradecanoic acid, hexadecanoic acid, octadecanoic acid, eicosanoic acid, 2-ethyl hexanoic acid, 2-ethyl-2-methyl hexanoic acid, 3,5,5-trimethyl hexanoic acid, neo-tridecanoic acid, isopalmitic acid, isostearic acid and a mixture thereof.
8. The compound of claim 1 wherein R is the hydrocarbon residue of lanolic acid.
9. The compound of claim 1 wherein $R'_1$ is alkyl and is selected from the group consisting of octyl, nonyl, decyl, undecyl, dodecyl, tridecyl, tetradecyl, hexadecyl and a mixture thereof.
10. The compound of claim 1 wherein $R'_1$ is alkyl and is the hydrocarbon residue of R'—OH alcohol selected from the group consisting of octanol, decanol, dodecanol, tetradecanol, hexadecanol, octadecanol, eicosanol, 2-ethyl hexanol, 2,2-dimethyl hexanol, 3,7-dimethyl octanol, 2-hexyl decanol, 2-octyl dodecanol, isostearyl alcohol and a mixture thereof.
11. The compound of claim 1 wherein R' is the hydrocarbon residue of an oxo alcohol.
12. The compound of claim 1 wherein $R'_1$ is alkyl and is the hydrocarbon residue of a R'—COOH acid selected from the group consisting of octanoic acid, decanoic acid, dodecanoic acid, tetradecanoic acid, hexadecanoic acid, octadecanoic acid, eicosanoic acid, 2-ethyl hexanoic acid, 2-ethyl-2-methyl hexanoic acid, 3,5,5-trimethyl hexanoic acid, neo-tridecanoic acid, isopalmitic acid, isostearic acid and a mixture thereof.
13. The compound of claim 1 having a molecular weight between about 300 and 5,000.
14. The compound of claim 1 wherein $A_1$, R, $R'_1$, X, $Y_1$ and n are selected from the following sets of values:
(a) $A_1$ is hydrogen, R is pentadecyl, $R'_1$ is 2-ethyl hexyl, X is

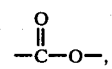

$Y_1$ is oxygen and n=7;
(b) $A_1$ is hydrogen, R is the hydrocarbon residue of isostearyl alcohol, $R'_1$ is octyl, X is oxygen, $Y_1$ is —$CH_2$— and n=2.3;
(c) $A_1$ is hydrogen, R is the hydrocarbon residue of branched chain hexadecyl alcohol, $R'_1$ is 2-ethyl hexyl, X and $Y_1$ are both oxygen and n=4;
(d) $A_1$ is hydrogen, R is the hydrocarbon residue of isostearyl alcohol, $R'_1$ is 2-ethyl hexyl, X and $Y_1$ are both oxygen and n=6;
(e) $A_1$ is hydrogen, R is the hydrocarbon residue of branched chain hexadecyl alcohol, $R'_1$ is a mixture of decyl and dodecyl, X is oxygen, $Y_1$ is —$CH_2$— and n=3;

(f) $A_1$ is hydrogen, R is 2-ethyl hexyl, $R'_1$ is a mixture of dodecyl and tetradecyl, X and $Y_1$ are both oxygen and n=6;

(g) $A_1$ is hydrogen; $R'_1$ is 2-ethyl hexyl, X and $Y_1$ are both oxygen and n=10;

(h) $A_1$ is hydrogen, R is 2-ethyl hexyl, $R'_1$ is a mixture of undecyl, dodecyl, tridecyl and tetradecyl, X is oxygen, $Y_1$ is —$CH_2$— and n=5;

(i) $A_1$ is hydrogen, R is pentadecyl, $R'_1$ is 2-ethyl hexyl, X is

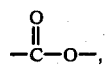

$Y_1$ is oxygen and n=2;

(j) $A_1$ is hydrogen, R is a mixture of hexadecyl and octadecyl, $R'_1$ is 2-ethyl hexyl, X and $Y_1$ are both oxygen and n=2;

(k) $A_1$ is hydrogen, R is the hydrocarbon residue of isostearic acid, $R'_1$ is 2-ethyl hexyl, X is

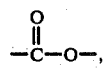

$Y_1$ is oxygen and n=2.5;

(l) $A_1$ is hydrogen, R is dodecyl, $R'_1$ is a mixture of undecyl, dodecyl, tridecyl and tetradecyl, X is oxygen, $Y_1$ is —$CH_2$— and n=5;

(m) $A_1$ is hydrogen, R is octadecyl, $R'_1$ is a mixture of undecyl, dodecyl, tridecyl and tetradecyl, X is oxygen, $Y_1$ is —$CH_2$— and n=1.3;

(n) $A_1$ is hydrogen, R is a mixture of hexadecyl and octadecyl, $R'_1$ is the hydrocarbon residue of isostearyl alcohol, X and $Y_1$ are both oxygen and n=5;

(o) $A_1$ is hydrogen, R is the hydrocarbon residue of lanolic acid, $R'_1$ is $C_8H_{17}$, X is

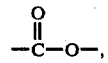

$Y_1$ is —$CH_2$— and n=3;

(p) $A_1$ is hydrogen, R is $C_{16}H_{33}$, $R'_1$ is a mixture of $C_{12}H_{25}$ and $C_{14}H_{29}$, X and $Y_1$ are both oxygen and n=8;

(q) $A_1$ is hydrogen, R is a 50:50 mixture of $C_{16}H_{33}$ and $C_{18}H_{37}$, $R'_1$ is a mixture of $C_{10}H_{21}$ and $C_{12}25$, X is oxygen, $Y_1$ is —$CH_2$— and n=5;

(r) $A_1$ is hydrogen, R is the hydrocarbon residue of lanolin alcohol, $R'_1$ is a mixture of $C_{10}H_{21}$ and $C_{12}H_{25}$, X is oxygen, $Y_1$ is —$CH_2$— and n=3;

(s) $A_1$ is hydrogen, R is the hydrocarbon residue of lanolin alcohol, $R'_1$ is a mixture of $C_{10}H_{21}$ and $C_{12}H_{25}$, X is oxygen, $Y_1$ is —$CH_2$— and n=5;

(t) $A_1$ is hydrogen, R is the hydrocarbon residue of lanolin alcohol, $R'_1$ is a mixture of $C_{10}H_{21}$ and $C_{12}H_{25}$, X is oxygen, $Y_1$ is —$CH_2$— and n=1.5;

(u) $A_1$ is a mixture of hydrogen and

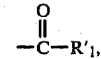

R is 2-octyl decyl, $R'_1$ is the hydrocarbon residue of isostearic acid, X is oxygen, $Y_1$ is

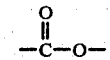

and n=5;

(v) $A_1$ is a mixture of hydrogen and

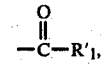

R is 2-octyl decyl, $R'_1$ is the hydrocarbon residue of lauric acid, X is oxygen,

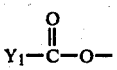

and n=5;

(w) $A_1$ is a mixture of hydrogen and

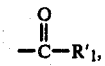

R is a mixture of alkyl radicals containing 11 to 15 carbon atoms, $R'_1$ is the hydrocarbon residue of 2-ethyl hexanoic acid, X is oxygen, $Y_1$ is

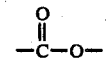

and n=4;

(x) $A_1$ is a mixture of hydrogen and

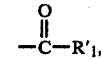

R is a mixture of hexadecyl and octadecyl, $R'_1$ is the hydrocarbon residue of 2-ethyl hexanoic acid, X is oxygen, $Y_1$ is

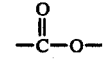

and n=6;

(y) $A_1$ is a mixture of hydrogen and

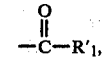

R is a mixture of alkyl radicals containing 11 to 15 carbon atoms, $R'_1$ is the hydrocarbon residue of lauric acid, X is oxygen, $Y_1$ is

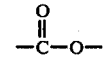

and n=4 and (z) $A_1$ is a mixture of hydrogen and

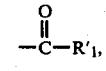

R is a mixture of hexadecyl and octadecyl, $R'_1$ is the hydrocarbon residue of 2-ethyl hexanoic acid, X is oxygen, $Y_1$ is

and n=2.

15. A cosmetic excipient in the form of an oil or wax comprising a member selected from the group consisting of (a) a compound having the formula

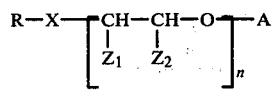

wherein

R is selected from the group consisting of alkyl having 7 to 20 carbon atoms, the hydrocarbon residue of lanolin when X is oxygen and the hydrocarbon residue of lanolic acid when X is

one of $Z_1$ and $Z_2$ represents —$CH_2$—Y—R' and the other represents hydrogen;

X represents a member selected from the group consisting of oxygen and carbonyloxy having the formula

linked to R through the free bond of the carbon atom of the carbonyloxy group;

Y represents a member selected from the group consisting of —$CH_2$—, oxygen and carbonyloxy of the formula

linked to R' through the free bond of the carbon atom of said carbonyloxy group;

R' represents alkyl having 3–20 carbon atoms with the proviso that R' can have different values in the said repeating units of a given compound of said formula in (a);

A is selected from the group consisting of hydrogen and when Y is carbonyloxy, a mixture of hydrogen and

wherein R' has the meaning given above; and n is a decimal or whole number greater than 1 and lower than or equal to 10; and (b) a mixture of the compounds defined in (a).

16. The cosmetic excipient of claim 15 wherein at least one of R and R' is branched chain alkyl.

17. The cosmetic excipient of claim 15 wherein R is the hydrocarbon residue of a R–OH alcohol selected from the group consisting of octanol, decanol, dodecanol, tetradecanol, hexadecanol, octadecanol, eicosanol, 2-ethyl hexanol, 2,2-dimethyl hexanol, 3,7-dimethyl octanol, 2-hexyl decanol, 2-octyl decanol, 2-octyl dodecanol, isostearyl alcohol and a mixture thereof.

18. The cosmetic excipient of claim 15 wherein R is the hydrocarbon residue of an oxo alcohol.

19. The cosmetic excipient of claim 15 wherein R is the hydrocarbon residue of lanolin alcohol.

20. The cosmetic excipient of claim 15 wherein R is a hydrocarbon residue of the R–COOH acid selected from the group consisting of octanoic acid, decanoic acid, dodecanoic acid, tetradecanoic acid, hexadecanoic acid, octadecanoic acid, eicosanoic acid, 2-ethyl hexanoic acid, 2-ethyl-2-methyl hexanoic acid, 3,5,5-trimethyl hexanoic acid, neo-tridecanoic acid, isopalmitic acid, isostearic acid or mixture thereof.

21. The cosmetic excipient of claim 15 wherein R is the hydrocarbon residue of lanolic acid.

22. The cosmetic excipient of claim 15 wherein R' is alkyl and is selected from the group consisting of propyl, butyl, pentyl, hexyl, heptyl, octyl, nonyl, decyl, undecyl, dodecyl, tridecyl, tetradecyl, hexadecyl and a mixture thereof.

23. The cosmetic excipient of claim 15 wherein R' is alkyl and is the hydrocarbon residue of a R'–OH alcohol selected from the group consisting of isopropanol, t-butanol, isopentanol, 2-ethyl butanol, 2-methyl pentanol, 4-methyl pentanol, octanol, decanol, dodecanol, tetradecanol, hexadecanol, octadecanol, eicosanol, 2-ethyl hexanol, 2,2-dimethyl hexanol, 3,7-dimethyl octanol, 2-hexyl decanol, 2-octyl decanol, 2-octyl dodecanol, isostearyl alcohol and a mixture thereof.

24. The cosmetic excipient of claim 15 wherein R' is a hydrocarbon residue of an oxo alcohol.

25. The cosmetic excipient of claim 15 wherein R' is alkyl and is the hydrocarbon residue of a R'COOH acid selected from the group consisting of octanoic acid, decanoic acid, tetradecanoic acid, hexadecanoic acid, octadecanoic acid, eicosanoic acid, 2-ethyl hexanoic acid, 2-ethyl-2-methyl hexanoic acid, 3,5,5-trimethyl hexanoic acid, neo-tridecanoic acid, isopalmitic acid, isostearic acid and a mixture thereof.

26. A cosmetic composition containing the cosmetic excipient of claim 15 in an amount of 0.15 to 70 percent by weight of the total weight of said composition.

27. The cosmetic composition of claim 26 wherein said excipient is present in an amount of 0.2 to 50 percent by weight of the total weight of said composition.

28. The cosmetic composition of claim 26 comprising a lip rouge, deodorant, eyelid liner, eye shadow, cream, liquid dye foundation, makeup remover milk, anti-solar milk, bath oil or product for imparting a shiny appearance to hair.

* * * * *